United States Patent

Roe et al.

[11] Patent Number: 5,917,585
[45] Date of Patent: Jun. 29, 1999

[54] METHOD FOR DISTINGUISHING PEN FROM OTHER MATERIALS

[76] Inventors: Mitchell Gregg Roe, 306 Crooked Oak Ct., Franklin, Tenn. 37067; Garry R. Kenny, Rte. 1, 6299 McDaniel Rd., College Grove, Tenn. 37046

[21] Appl. No.: 08/934,685

[22] Filed: Sep. 22, 1997

[51] Int. Cl.⁶ .................................................. G01N 21/00
[52] U.S. Cl. ............................................................ 356/73
[58] Field of Search ........................... 356/73, 364–369, 356/370, 240, 428; 350/223 R, 225; 269/524, 580, 576–577, 579, 588; 382/142, 143; 348/91, 127

[56] References Cited

U.S. PATENT DOCUMENTS

| | | | |
|---|---|---|---|
| 5,150,307 | 9/1992 | McCourt et al. | 364/478 |
| 5,263,591 | 11/1993 | Taormina et al. | 209/630 |
| 5,318,172 | 6/1994 | Kenny et al. | 209/524 |
| 5,502,559 | 3/1996 | Powell et al. | 356/73 |
| 5,555,984 | 9/1996 | Sommer, Jr. et al. | 209/580 |
| 5,603,413 | 2/1997 | Mitchum, Jr. | 209/580 |
| 5,675,416 | 10/1997 | Campbell et al. | 356/367 |
| 5,695,039 | 12/1997 | Driscoll et al. | 194/212 |

OTHER PUBLICATIONS

"A Two–Colour Near–Infrared Sensor for Sorting Recycled Plastic Waste" Oct. 24, 1994.

*Primary Examiner*—Frank G. Font
*Assistant Examiner*—Michael P. Stafira
*Attorney, Agent, or Firm*—Waddey & Patterson; Edward D. Lanquist, Jr.

[57] ABSTRACT

In the present invention, a system and method are disclosed for distinguishing PEN from other types of materials. The method and system discloses an electromagnetic radiation source which transmits electromagnetic radiation to an object. The electromagnetic radiation either passing through an object or rejecting from an object is then measured to determine the amount of penetrating or reflecting electromagnetic radiation. This amount of penetrating or reflecting electromagnetic radiation is then measured to classify the item by type.

24 Claims, 9 Drawing Sheets

METHOD FOR DISTINGUISHING PEN FROM OTHER MATERIALS

BACKGROUND OF THE INVENTION

The present invention relates generally to a material sorting device and more particularly to a device for distinguishing polyethylene naphthalate from other materials such as polyethylene terephthalate.

It will be appreciated by those skilled in the art that recycling and reclaiming of materials is very critical to the world's ecology. As a result, there have been several attempts to sort one type of material from another. In the past, these materials have related to glass, aluminum, and plastic bottles. Unfortunately, none of these devices dose a method of distinguishing PEN from any other material. PEN is a new type of plastic that is being adopted by many plastic manufacturers. Therefore, no one has performed the experimentation necessary to sort PEN from other types of material.

What is needed, then, is a system for sorting PEN from other types of materials. This needed system must be capable of sorting PEN from PET. This needed system must also be capable of sorting items by content of PEN. This system must be economical. This system is presently lacking in the prior art.

SUMMARY OF THE INVENTION

In the present invention, a system and method are disclosed for distinguishing PEN from other types of materials. The method and system discloses an electromagnetic radiation source which transmits electromagnetic radiation to an object. The electromagnetic radiation either passing through an object or reflecting from an object is then measured to determine the amount of penetrating or reflecting electromagnetic radiation. This amount of penetrating or reflecting electromagnetic radiation is then measured to classify the item by type.

Accordingly, one object of the present invention is to provide a system and method for distinguishing PEN from other types of materials.

Another object of the present invention is to classify items containing PEN by content.

Another object of the present invention is to provide a method and system which is economical and efficient.

Another object of the present invention is to provide a system which is very accurate.

DESCRIPTION OF THE PREFERRED EMBODIMENTS

Figure 1:
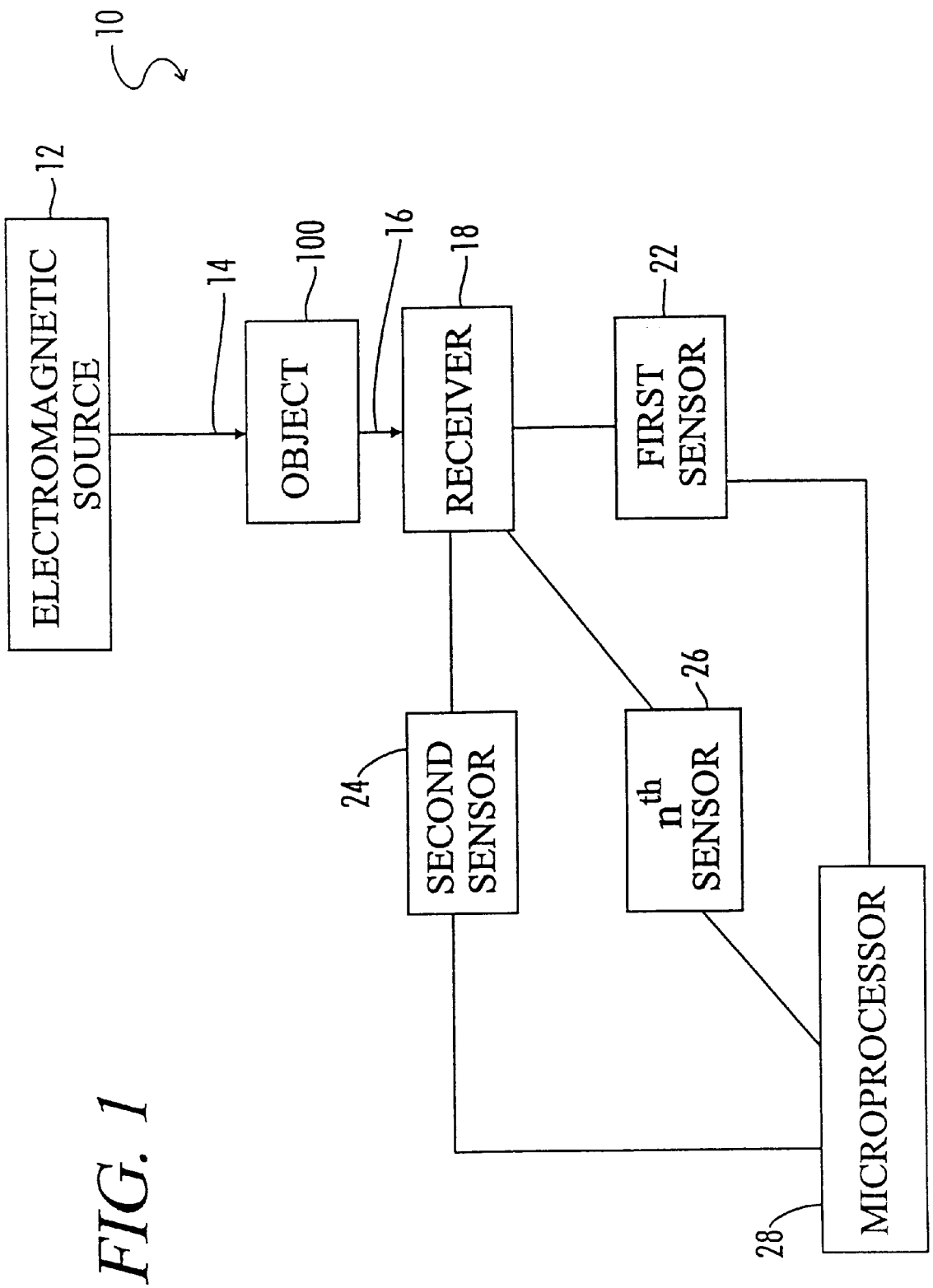
FIG. 1 is a block diagram of one embodiment of the system and method of the present invention.

Referring now to FIG. 1, there is shown generally at 10 the system and method for distinguishing PEN from other types of materials. Electromagnetic source 12 transmits electromagnetic radiation 14 to object 100. The electromagnetic radiation either penetrating or reflecting from object 100 is designated by arrow 16 which refers to the penetrating or reflecting electromagnetic radiation. Receiver 18 receives penetrating or reflecting electromagnetic radiation directed into first sensor 22, second sensor 24, and/or $n^{th}$ sensor 26. Sensor readings are then electronically fed into microprocessor 28 where the various sensor readings can be evaluated or compared.

Figure 2:
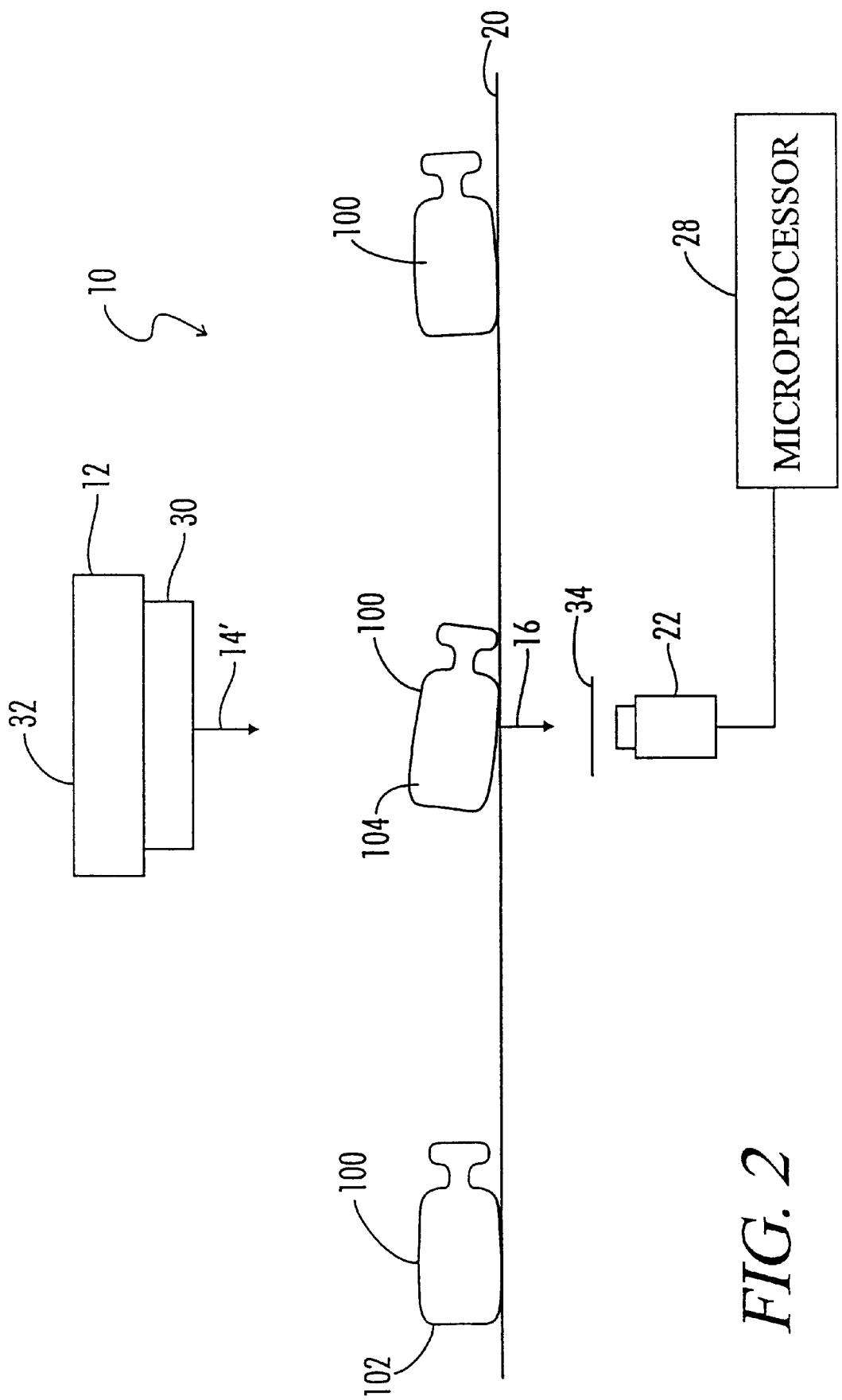
FIG. 2 is a side view of one embodiment of the present invention.

Referring now to FIG. 2, there is shown generally at 10 the system and method of the present invention in one of the simplest forms. In this particular embodiment, electromagnetic source 12 is lamp 30' containing housing 32. In this particular embodiment, electromagnetic radiation 14' is in the band preferably of a wavelength range of 350 to 450. Electromagnetic radiation 14' is transmitted into object 100 which, in this embodiment, is either PET bottle 102 or PEN bottle 104. However, object 100 can be a combination of PEN bottle 104 and any other material. Visible electromagnetic radiation 14' passes through object 100 and becomes penetrating electromagnetic radiation 16. Penetrating electromagnetic radiation 16 is received by first sensor 22 which is electronically connected to microprocessor 28. Microprocessor 28 compares the readings taken by sensor 22 to determine whether the item is PEN or another type of material. In the preferred embodiment, first sensor 22 has first filter 34 which filters penetrating electromagnetic radiation 16 before it reaches first sensor 22. In the preferred embodiment, filter 34 is narrow band interference filter of substantially 380 nanometers. If the amount of penetrating electromagnetic radiation 16 is substantially less than the amount of electromagnetic radiation 14', microprocessor 28 classifies object 100 as PEN.

Figure 3:
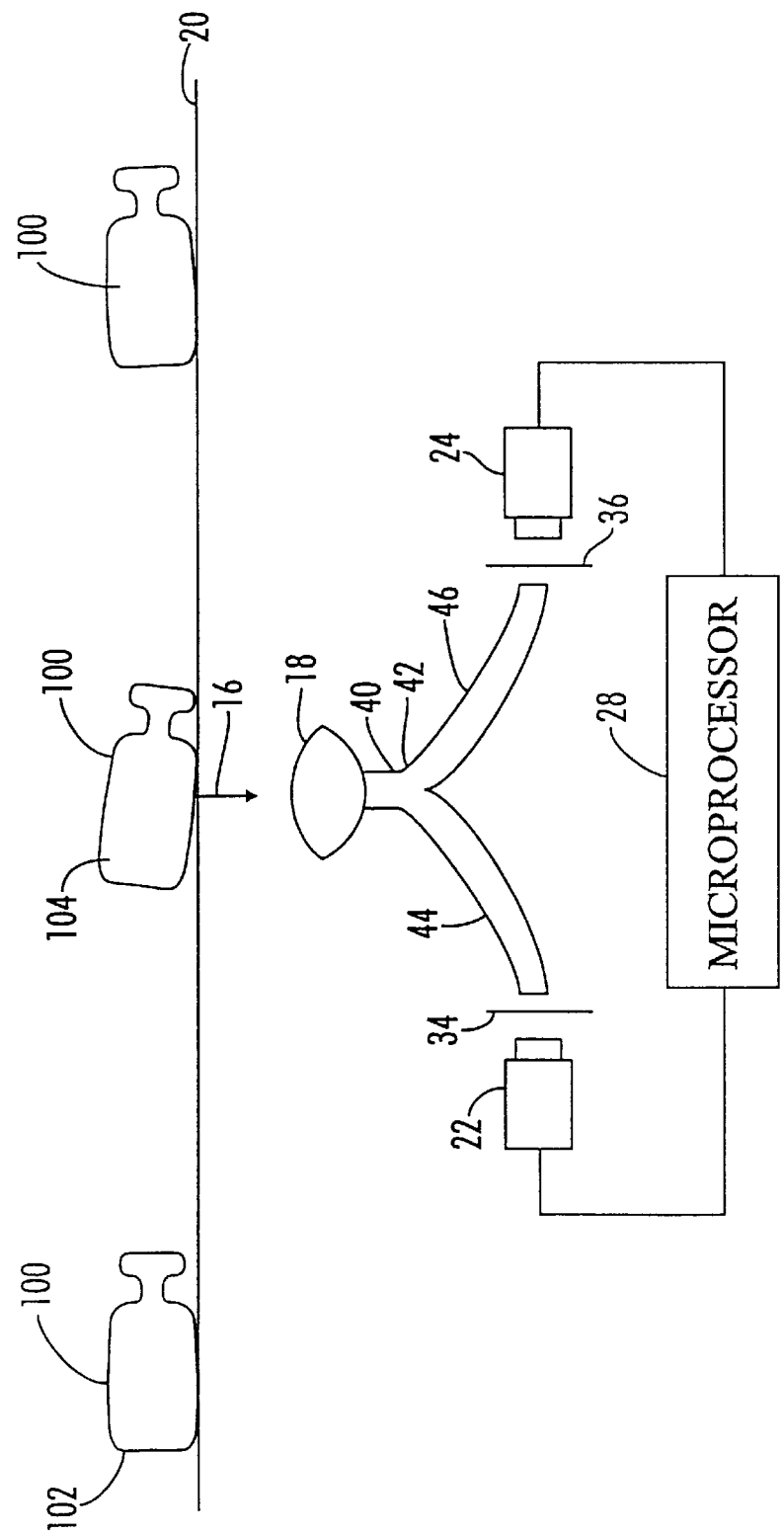
FIG. 3 is a side view of another embodiment of the present invention.

Referring now to FIG. 3, there is shown a slightly more complex method and system for distinguishing PEN from other types of materials. Like FIG. 2, electromagnetic source 12 uses lamp in housing 32. Electromagnetic radiation 14' is created by lamp and directed through object 100. In the preferred embodiment, objects 100 are either PET 102 or PEN 104. Objects 100 are presented along wear cover 20. The penetrating electromagnetic radiation 16 is received by receiver 18 which is preferably a plano-convex lens manufactured by Edmund Scientic. Receiver 18 transmits penetrating electromagnetic radiation 16 into splitter 40 which is preferably fiberoptic cable 42 of the type such as that manufactured by Cuda Products Corp. which directs penetrating electromagnetic radiation into first stream 44 and second stream 46. First stream 44 is preferably filtered by filter 34 which is preferably a 380 nanometer narrow band interference filter prior to transmitting penetrating electromagnetic radiation 16 into first sensor 22. Likewise, second stream 46 is preferably filtered using filter 36 which is preferably a narrow band interference filter of substantially 400 nanometers prior to being received by sensor 24. Sensors are again electronically connected to microprocessor 28. Microprocessor then takes readings from first sensor 22 and divides them by the reading of sensor 24. If this ratio approaches 1, microprocessor 28 classified object 100 as PET. If the ratio approaches zero, the object is classified as PEN.

Figure 4:
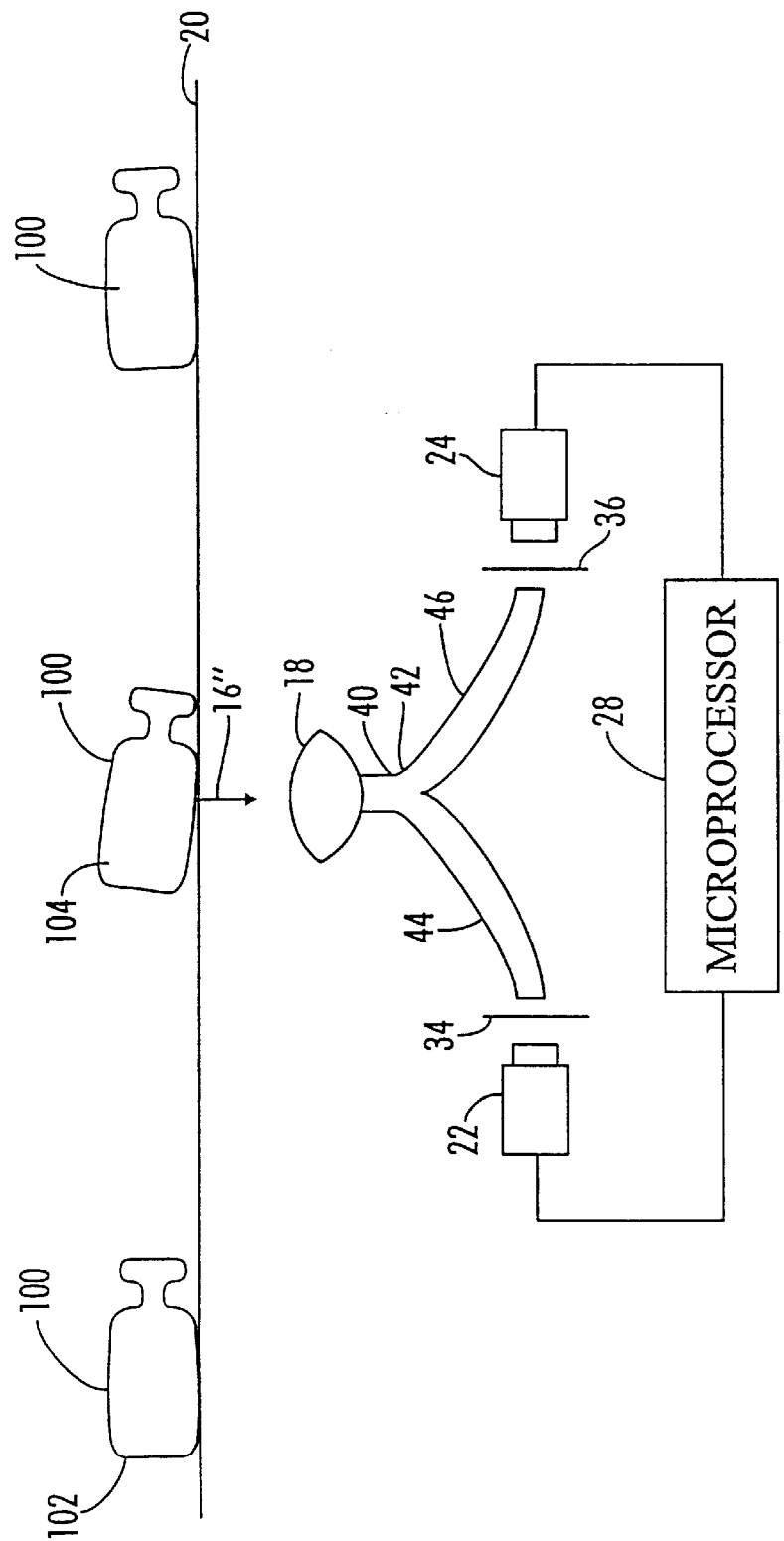
FIG. 4 is a side view of another embodiment of the present invention.

Referring now to FIG. 4, there is shown generally at 10 another embodiment of the system and method for distinguishing PEN from other materials of the present invention. In this particular embodiment, lamp 30 transmits infrared radiation 14" preferably of a wavelength of 1600 to 1700 nanometers through object 100. This then becomes penetrating electromagnetic radiation 16". Receiver 18 receives penetrating eared penetrating radiation which directs transmitted infrared radiation to splatter 40 which splits transmitted infrared radiation into first path 44 and second path 46. In the preferred embodiment, first filter 34 is substantially 1660 nanometers whereas second filter 36 is substantially 1670 nanometers. The amount of transmitted energy received by first sensor 22 is divided by the amount of electromagnetic radiation received by second sensor 24 by microprocessor 28. If the number is high, the material is classified as PEN.

Instead of using filters 34, 36, electromagnetic source 12 can actually consist of alternating LEDs which transmit electromagnetic radiation 14 at an initial wavelength of substantially 1660 and a second set of LEDs which transmit electromagnetic radiation 14 at substantially 1670 nanometers.

Similarly, in FIG. 2, visible light lamp 30' can actually consist of LEDs of differing wavelengths so that instead of splitting the single signal as shown in FIG. 3, LEDs emitting electromagnetic radiation at wavelengths of 380 and 400 can be received by first sensor 22 without filter 34. These alternating signals read by first sensor 22 can be analyzed by microprocessor 28 to perform the ratio discussed in, connection with FIG. 3.

Figure 5:
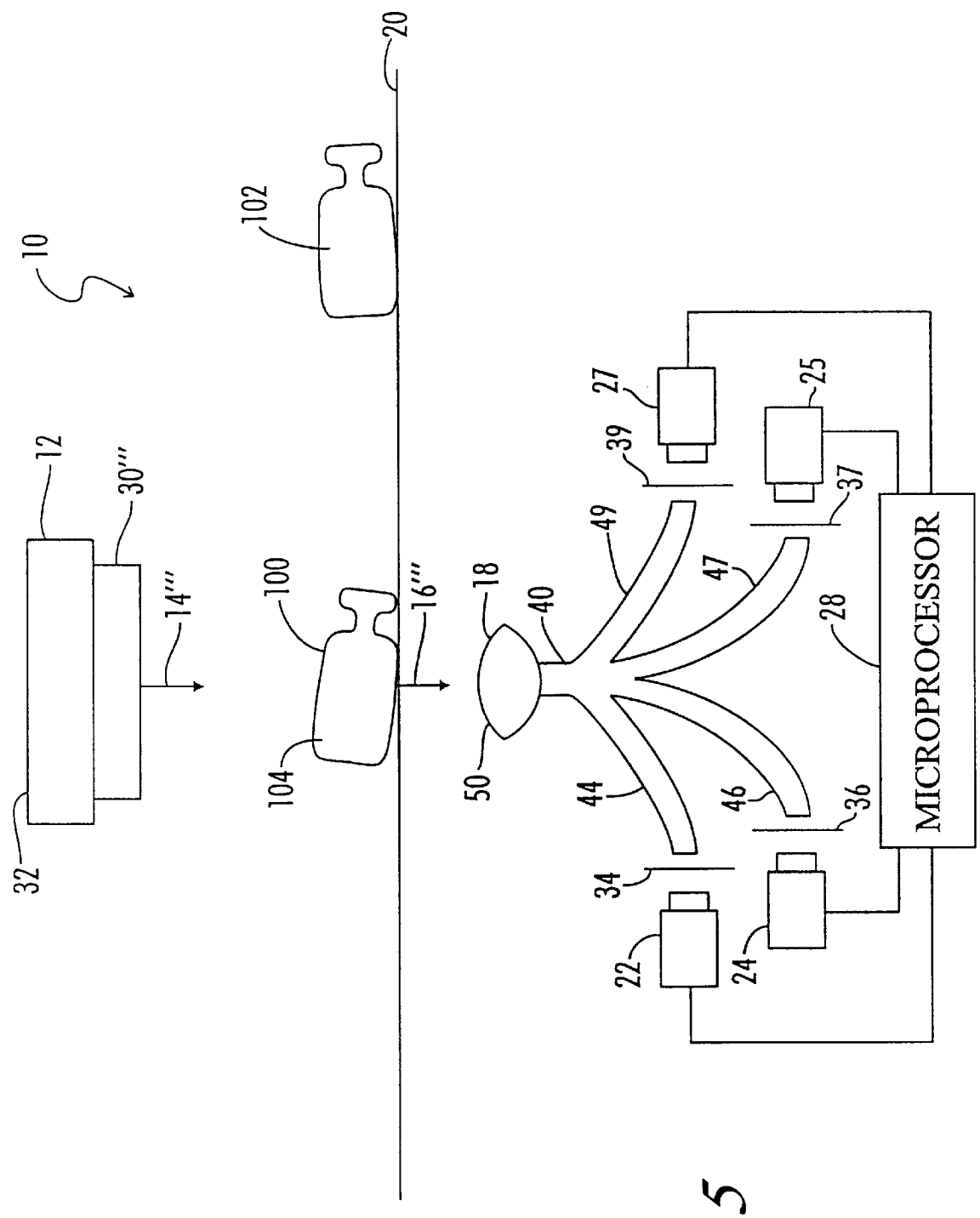
FIG. 5 is a side view of another embodiment of the present invention.

Referring now to FIG. 5, there is shown still another embodiment of the present invention. In this particular embodiment, electromagnetic source 12 is broad band lamp 30''' in housing 32. Lamp 30''' transmits electromagnetic radiation 14 through objects 100 which are preferably PEN 104 or PET 102. Penetrating broad band radiation 16''' is received by receiver 18 which is preferably lens 50 and directed into splitter 40 which splits penetrating broad band radiation into first stream 44, second stream 46, third stream 47, and fourth stream 49. Streams 44, 46, 47, and 49 are received by first sensor 22, second sensor 24, third sensor 25, and fourth sensor 27. In the preferred embodiment, first stream 44 and filtered by first filter 34 which is preferably 380 nanometers. Second stream 46 is filtered by second filter 36 which is preferably 390 nanometers. Third stream 47 is filtered by third filter 37 of substantially 430 nanometers. Fourth stream 49 is filtered by fourth stream 39 of substantially 900 nanometers. The signals from sensors 22, 24, 25, and 27 are electronically fed into microprocessor 28. Microprocessor 28 evaluates the signals as follows:

| Method | Wavelengths | Algorithm |
| --- | --- | --- |
| Transmission | 380 | low ⇒ PEN |
| Transmission | 380,400 | 380/400 ≅ 1 ⇒ PET, |
| | | 380/400 low ⇒ PEN |
| Transmission | 1660,1670 | 1660/1670 > 1 ⇒ PET |
| Transmission | 380,390,430,400 | all about equal ⇒ PET |
| | | 380/390 and 390/430 determine PEN level |
| Fluorescence | ≧380 | strong fluorescence ⇒ PEN |
| Fluorescence | 390,425 | 390/425 ≧ 0.4 ⇒ PEN |
| | | also estimates PEN level |

Figure 6:
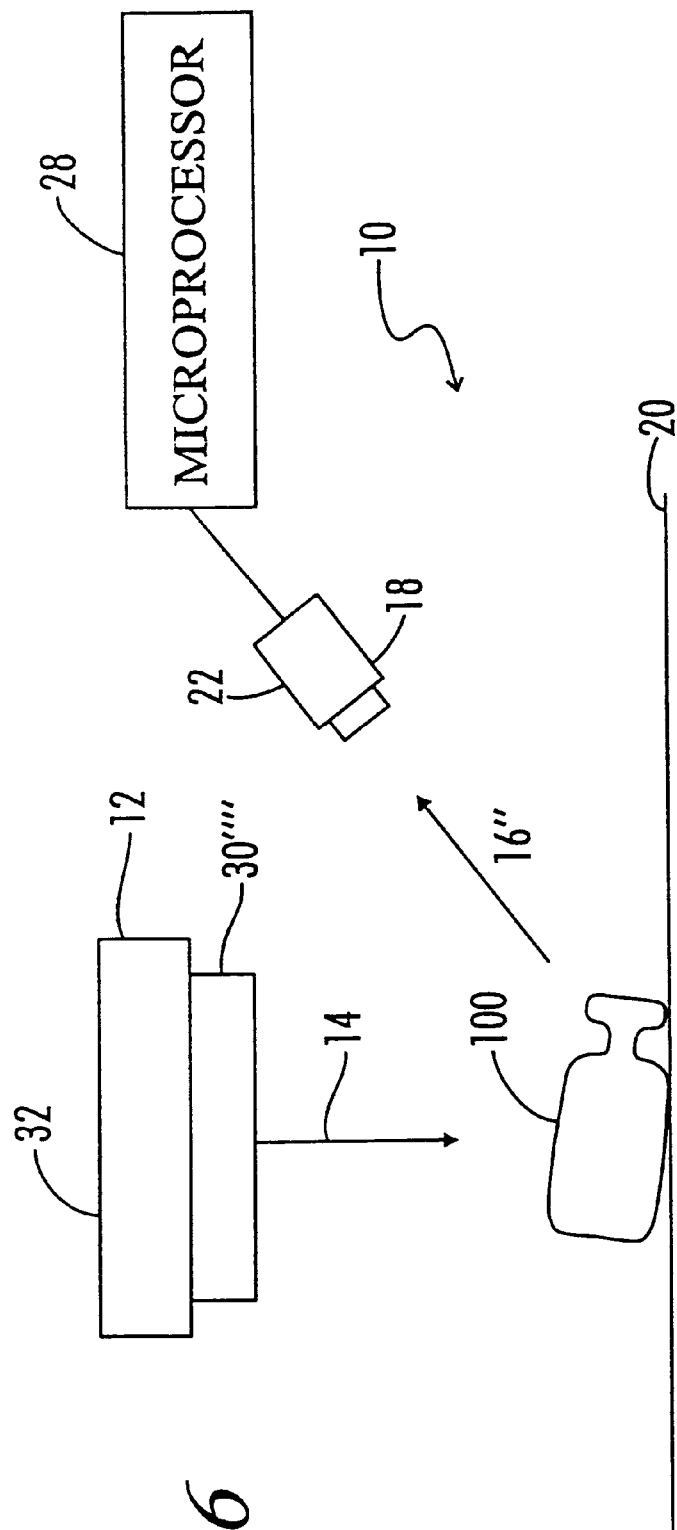
FIG. 6 is a side view of another embodiment of the present invention.

Referring now to FIG. 6, there is shown generally at 10 still another embodiment of the system and method of the present invention. In FIG. 6, electromagnetic source 12 is black light lamp 30''' having a wavelength of substantially 365 nanometers. Lamp 30'''' is housed in housing 32. Lamp 30'''' creates black light transmitted electromagnetic radiation 14 which is bounced off of object 100 and induces fluorescent electromagnetic radiation 16". Fluorescent electromagnetic radiation 16 is received by receiver 18 which is preferably received by first sensor 22. Signal from first sensor 22 is fed into microprocessor 28 and evaluated. If the amount of fluorescent electromagnetic radiation 16" is large, then the object is classified as PEN.

Referring now to FIGS. 2–7, objects 100 preferably reside upon wear cover 20. Wear cover 20 is preferably tilted so that the bottles will pass along wear cover 20.

Figure 7:
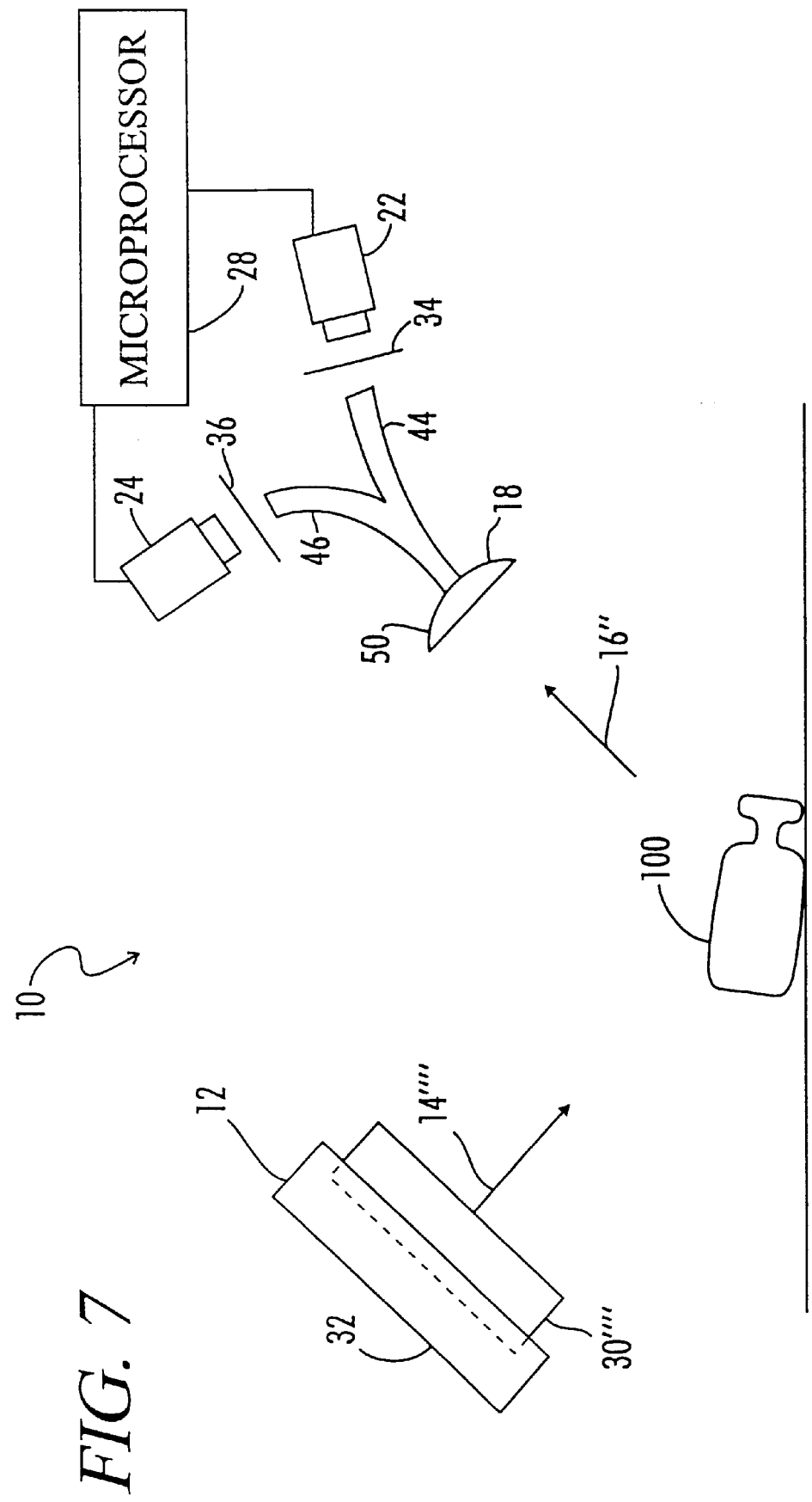
FIG. 7 is a side view of another embodiment of the present invention.

Referring now to FIG. 7, there is shown generally at 10 still another embodiment of the system and method of the present invention. In this particular embodiment, electromagnetic source 12 is again black light lamp 30'''' housed in housing 32. Transmitted electromagnetic radiation is black light 14'''' of substantially 365 nanometers. Transmitted black light 14'''' bounces off of object 100 and induces fluorescent electromagnetic radiation 16''''. Fluorescent electromagnetic radiation is received by receiver 18 which is preferably lens 50 before being sent into splitter 40 which is preferably fiberoptic cable 42 having first stream 44 and second stream 46. First stream 44 is filtered using first filter 34 of substantially 390 nanometers before passing into first sensor 22. Likewise, second stream 46 is preferably filtered using second filter 36 of substantially 425 nanometers before being received by second sensor 24. First sensor 22 and second sensor 24 are electronically connected to microprocessor 28 which evaluates readings from first sensor 22 and second sensor 24. The signal received by first sensor 22 is divided by the signal received: by second sensor 24. If the ratio is 0.4 or higher, then the item is classified as PEN. If the ratio is 0.2, then the object is classified as PET.

Figure 8A:
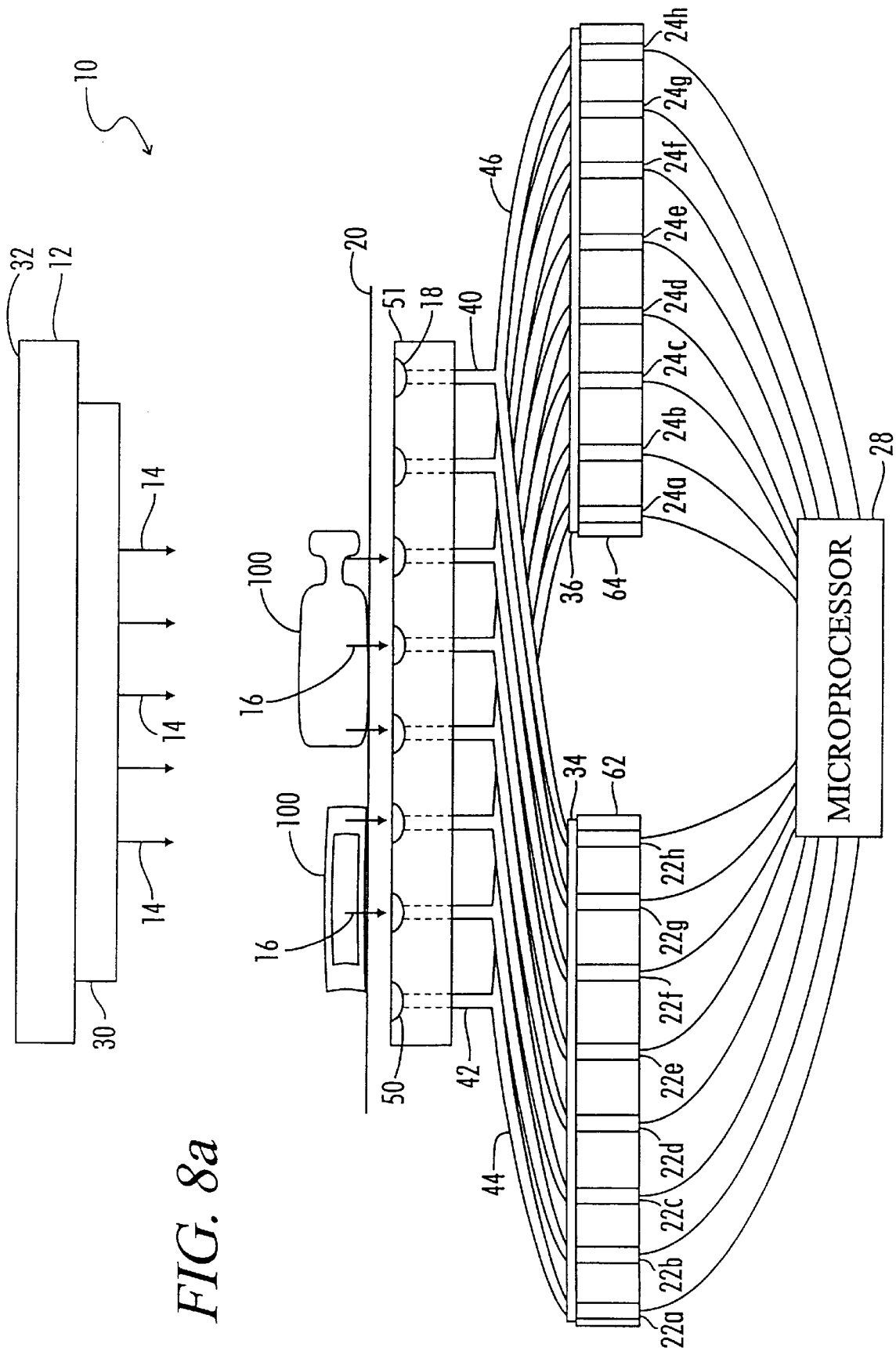
FIGS. 8a–c are drawings showing a random sort embodiment of the present application.
Figure 8B:
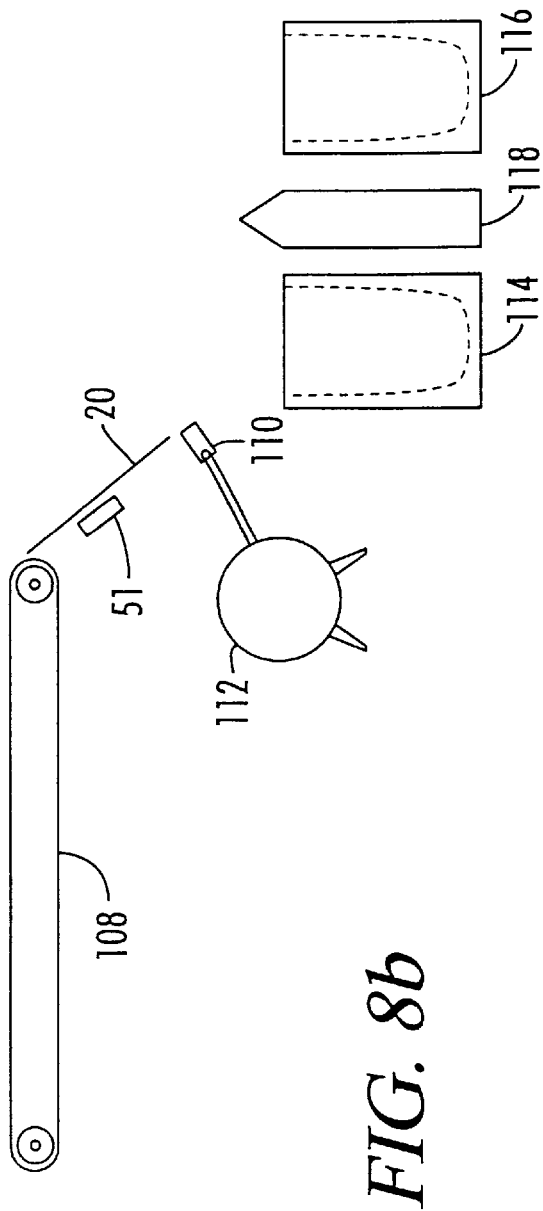
Figure 8C:
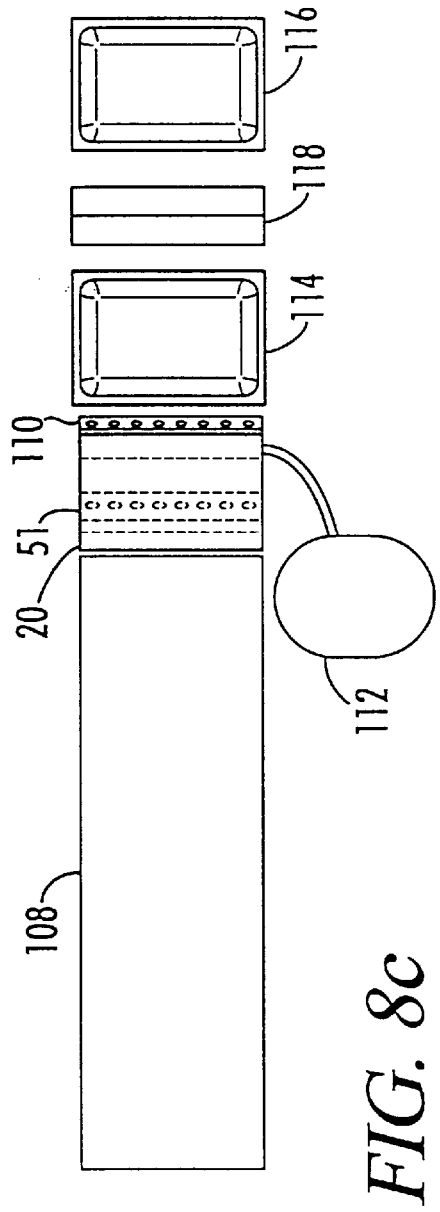

Referring now to FIG. 8a–c, there is shown generally at 10, a multiple sensor embodiment of the present invention. Electromagnetic radiation 14 is created as described above using electromagnetic source 12 which is preferably lamp 30 in housing 32. Some of the differing types of electromagnetic radiation are discussed above. Objects 100 travel across wear cover 20 and receive electromagnetic radiation 14 which is, in is embodiment, transmitted through object 100 so that penetrating electromagnetic radiation 16 is received by receiver 18 which is in the embodiment lens 50 housed in lens board 51. Splitter 40 which is preferably fiberoptic cable 42 splits each received amount of penetrating electromagnetic radiation 16 into first stream 44 and second stream 46. Each stream contains is required wave length band width. However, additional streams (47, 49 in other Figures) can also be created. First stream 44 from each splitter 40 is directed through first filter 34 into a corresponding first sensor 22a–h in first sensor array 62 which in turn are electronically connected to microprocessor 28. Second stream 46 from each spatter 40 is directed through second filter 36 into a corresponding second sensor 24a–h in second sensor array 64 which in turn are electronically connected to microprocessor 28. As objects 100 are classified by microprocessor 28, air array 110 (or some other ejection mechanism) powered by compressor 112 ejects the bottles to be ejected into second bin 116 over divider 118 otherwise objects 100 which are not to be ejected fall into first bin 114. Objects 100 can be fed by conveyor 108.

The simplest way to determine the existence of PEN is to use a transmitted electromagnetic radiation at substantially 380 nanometers. If the amount of electromagnetic radiation transmitted is low, then the item can be classified as PEN.

A second method is to use transmitted electromagnetic radiation measured at 380 nanometers and 400 nanometers.

If the ratio of the amount of transmitted radiation at 380 nanometers when divided by the amount of electromagnetic radiation transmitted at 400 nanometers approaches 1, the object can be classified as PET. Conversely, when the amount of electromagnetic radiation measured at 380 nanometers divided by the amount of electromagnetic radiation transmitted at 400 nanometers is low, the object can be classified as PEN.

A third method is to use infrared frequencies measured at wave lengths of 1660 nanometers and 1670 nanometers. If the ratio of transmitted electromagnetic radiation measures 1660 nanometers divided by the amount of transmitted electromagnetic radiation measured at 1670 nanometers is greater than 1, then the object can be classified as PEN.

The fourth method is to measure the amount of transmitted electromagnetic radiation measured at 380 nanometers, 390 nanometers, 430 nanometers, and 900 nanometers. If all of these are approximately equal, then the object can be classified as PET. Conversely, if the amount of penetrating electromagnetic radiation measured at 380 nanometers divided by the transmitted electromagnetic radiation transmitted at 390 nanometers approaches 0.5, the item is approximately 5% PEN. If the amount of penetrating electromagnetic radiation measured at 390 nanometers divided by the transmitted electromagnetic radiation transmitted at 430 nanometers approaches 0.25, the item is approximately 25% PEN. If the amount of penetrating electromagnetic radiation measured at 380 and 390 nanometers divided by the radiation measured at 900 nanometers approaches 0.2 or less, the item is 100% PEN.

One of the reflective or fluorescent method is to use a wavelength greater than or substantially equal to 380 nanometers. If there is strong fluorescence, then the object can be classified as PEN.

A second fluorescence method is to use wavelengths of 390 nanometers and 425 nanometers. If the ratio of fluorescence at 390 nanometers divided by fluorescence at 425 nanometers is greater than or is equal to 0.4, then the object is to be classified as PEN. This system can also be used to estimate the actual PEN level.

As soon as one develops a system which uses a dual separation system, certain critical factors must be analyzed such as slides, angle, bottle speed, splitter position, and other mechanical features that depend upon the orientation of the machine.

Thus, although there have been described particular embodiments of the present invention of a new and useful System For Distinguishing PEN From Other Materials, it is not intended that such references be construed as imitations upon the scope of this invention except as set forth in the following claims.

What is claimed is:

1. A method for classifying an object as either PEN objects or PET objects comprising the steps of:
    a. transmitting ultra-violet light through said object;
    b. receiving said ultra-violet light penetrating said object;
    c. measuring said received ultra-violet light; and
    d. classifying object as either PEN or PET.

2. The method of claim 1 wherein said ultra-violet light is measured at 380 nanometers.

3. A method for classifying an object as either PEN objects or PET objects comprising the steps of:
    e. transmitting ultra-violet light through said object;
    f. receiving said ultra-violet light penetrating said object;
    g. measuring said received ultra-violet light,
    h. wherein said ultra-violet light is measured at 380 nanometers;
    e. measuring said received visible light at 400 nanometers; and
    f. comparing the measured light at 380 nanometers with the measured light at 400 nanometers.

4. A method for classifying an object as either PEN objects or PET objects comprising the steps of:
    a. transmitting ultra-violet light through said object;
    b. receiving said ultra-violet light penetrating said object;
    c. measuring said received ultra-violet light,
    d. wherein said ultra-violet light is measured at 380 nanometers;
    e. wherein said transmitted light is transmitted using a first light source at 380 nanometers and a second light source at 400 nanometers.

5. The method of claim 1 further comprising filtering said light measured at 380 nanometers through a 380 nanometer filter.

6. The method of claim 2 further comprising filtering said light measured at 400 nanometers through a 400 nanometer filter.

7. The method of claim 2 further comprising splitting said penetrating light into a first signal and a second signal.

8. The method of claim 1 further comprising the steps of:
    a. measuring said received ultra-violet light at 390 nanometers;
    b. measuring said received visible light at 430 nanometers; and
    c. measuring said received infrared light at 900 nanometers.

9. The method of claim 8 further comprising the step of splitting said received visible light into a first stream, a second stream, a third stream, and a fourth stream prior to measuring.

10. The method of claim 9 further comprising the steps of filtering said split light prior to measuring.

11. The method of claim 10 wherein said filtering is performed by:
    a. a 380 nanometer filter for said first stream;
    b. a 390 nanometer filter for said second stream;
    c. a 430 nanometer filter for said third stream; and
    d. a 900 nanometer filter for said fourth stream.

12. The method of claim 1 wherein said visible light is transmitted by:
    a. a first light source of 380 nanometers;
    b. a second light source of 390 nanometers;
    c. a third light source of 430 nanometers; and
    d. a fourth light source of 900 nanometers.

13. The method of claim 2 further comprising transmitting said visible light with a 380 nanometer source, a 390 nanometer source, a 430 nanometer source, and a 900 nanometer source.

14. A method for classifying an object as either PEN objects or PET objects comprising the steps of:
    a. transmitting infrared light through said object;
    b. receiving said infrared light penetrating said object; and
    c. measuring said received infrared light at 1660 nanometers;
    d. measuring said received infrared light at 1670 nanometers; and
    e. comparing the measured light at 1660 nanometers with the measured light at 1670 nanometers.

15. The device of claim 14 wherein said transmitted infrared light is transmitted using a first infrared light source at 1660 nanometers and a second infrared light source at 1670 nanometers.

16. The method of claim 14 further comprising filtering said penetrating light measured at 1660 nanometers through a 1660 nanometer filter.

17. The method of claim 15 further comprising filtering said penetrating infrared light measured at 1670 nanometers through a 1670 nanometer filter.

18. The method of claim 15 further comprising splitting said penetrating light into a first signal and a second signal.

19. A method of classifying an object as PEN or PET comprising the step of:
   a. transmitting electromagnetic radiation to said object, said electromagnetic radiation selected from a group consisting of visible light, infrared light, or black light;
   b. receiving said electromagnetic radiation reflecting from said object or penetrating through said object;
   c. measuring said received electromagnetic radiation; and
   d. classifying said object as either PEN or PET.

20. A method of classifying an object as PEN or PET comprising the step of:
   a. transmitting electromagnetic radiation to said object, said electromagnetic radiation selected from a group consisting of visible light, infrared light, or black light;
   b. measuring fluorescence caused by said electromagnetic radiation;
   c. classifying said object as either PET or PEN.

21. The method of claim 20 wherein said electromagnetic radiation is transmitted at a wavelength of 380 nanometers.

22. The method of claim 20 wherein said electromagnetic radiation is transmitted at a wavelength of 390 nanometers and 425 nanometers.

23. The method of claim 20 wherein said electromagnetic radiation is measured at a wavelength of 380 nanometers.

24. The method of claim 20 wherein said electromagnetic radiation is measured at a wavelength of 390 nanometers and 425 nanometers.

* * * * *